(12) United States Patent
Philippe et al.

(10) Patent No.: US 6,391,863 B1
(45) Date of Patent: May 21, 2002

(54) USE OF CARBOHYDRATES FOR PROMOTING SKIN DESQUAMATION

(75) Inventors: Michel Philippe, Wissous; Catherine Ebenhan-Nappe, Aulnay-sous-Bois, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/043,914
(22) PCT Filed: Sep. 30, 1996
(86) PCT No.: PCT/FR96/01522
§ 371 Date: Jun. 16, 1998
§ 102(e) Date: Jun. 16, 1998
(87) PCT Pub. No.: WO97/12597
PCT Pub. Date: Apr. 10, 1997

(30) Foreign Application Priority Data

Oct. 4, 1995 (FR) ............................................ 95 11661

(51) Int. Cl.[7] ........................ A61K 31/70; C07H 15/00
(52) U.S. Cl. ........................ 514/62; 536/1.11; 536/4.1; 536/17.2; 536/17.3; 536/17.4; 536/18.4; 536/18.5; 536/18.6; 536/45; 536/55.1; 536/55.2; 536/55.3

(58) Field of Search ................................. 536/1.11, 4.1, 536/17.2, 17.3, 17.4, 18.4, 18.5, 18.6, 45, 55.1, 55.2, 55.3; 514/62

(56) References Cited

U.S. PATENT DOCUMENTS 4,767,750 A * 8/1988 Jacquet et al.
5,762,912 A * 6/1998 Eteve

FOREIGN PATENT DOCUMENTS

| FR | A-2 703 993 | | 10/1994 |
| WO | WO 92/05764 | | 4/1992 |
| WO | WO 93/10756 | * | 6/1993 |
| WO | WO 95/05155 | * | 2/1995 |

* cited by examiner

Primary Examiner—James O. Wilson
(74) Attorney, Agent, or Firm—Oblon, Spivak, McClelland, Maier & Neustadt, P.C.

(57) ABSTRACT

The use of carbohydrate derivatives in or for making a topical composition for promoting skin exfoliation is disclosed. The use of said composition of controlling intrinsic and extrinsic skin ageing, as well as a non-therapeutic skin treatment method for skin exfoliation, are also disclosed.

28 Claims, No Drawings

USE OF CARBOHYDRATES FOR PROMOTING SKIN DESQUAMATION

BACKGROUND OF THE INVENTION

1. Field of the Invention

The invention relates to the use of carbohydrate derivatives in or for the production of a cosmetic and/or dermatological composition for promoting skin desquamation and/or combating intrinsic and extrinsic skin ageing. It also relates to a non-therapeutic skin treatment process for desquamating the skin as well as to a non-therapeutic treatment process for cutaneous ageing.

2. Description of the Background

Cutaneous ageing resulting from effects of intrinsic or extrinsic factors on the skin is shown by the appearance of wrinkles and lines, by the yellowing of the skin which develops a blotchy look accompanied by the appearance of pigmentary spots, by the disorganization of the elastin and collagen fibres causing a loss of elasticity, of suppleness and of firmness and by the appearance of telangiectases.

Some of these signs of ageing are more particularly connected with intrinsic or physiological ageing, that is to say to "normal" ageing connected with age, although others are more specific to extrinsic ageing, that is to say ageing generally caused by the environment; more particularly photo-ageing due to exposure to the sun, to light or to any other radiation.

The invention is concerned with intrinsic or physiological ageing as well as with extrinsic ageing.

The changes in the skin due to intrinsic ageing are the consequence of a genetically programmed senescence in which endogenous factors intervene. This intrinsic ageing causes, especially, a slowing down of the renewal of the cells of the skin, which is essentially reflected by the appearance of clinical changes such as the reduction in the subcutaneous adipose tissue and the appearance of fine wrinkles or lines, and by histopathological changes such as an increase in the number and the thickness of the elastic fibres, a loss of vertical fibres in the membrane of the elastic tissue, and the presence of large irregular fibroblasts in the cells of this elastic tissue.

In contrast, extrinsic ageing results in clinical alterations such as thick wrinkles and the formation of a flabby and tanned skin, and in histopathological changes such as excessive accumulation of elastic matter in the upper dermis and degeneration of the collagen fibres.

Various agents intended for combating cutaneous ageing are known in the prior art.

Thus, the patent U.S. Pat. No. 4,603,146 describes the use of retinoic acid and of its derivatives in cosmetic compositions, for the purpose of combating cutaneous ageing.

However, many patents and publications (see, for example, the application EP-A-0413528) as well as numerous commercial cosmetic compositions teach the use of α-hydroxy acids such as lactic acid, glycolic acid or alternatively citric acid for treating cutaneous ageing.

Finally, β-hydroxy acids and more especially salicylic acid as well as its derivatives are known for their desquamating properties (see the documents WO-A-93/10756 and U.S. Pat. No. 4,767,750).

All these compounds have an action against ageing of the skin, consisting in desquamation, that is to say the elimination of "dead" cells situated at the surface of the stratum corneum. This desquamating property is also called, often wrongly, a keratolytic property. However, these compounds also have secondary effects, which consist of stinging, pulling, heating and redness, which are unpleasant for the user.

It is thus seen that the need exists for anti-ageing agents having an action which is at least as effective as that of the compounds of the prior art, but does not have their disadvantages.

On the other hand, Brysk (Cell and tissue research 253, 657–663, 1988; Expl. Cell Biol. 57, 60–66, 1989) has shown the role of glycoproteins in the cohesion of the stratum corneum. She has likewise demonstrated the inhibitory action of certain carbohydrates, in particular of aminocarbohydrates, with respect to the cohesion of the stratum corneum.

The Applicant has unexpectedly discovered that certain carbohydrate derivatives show a very significant inhibitory action on the cohesion of the stratum corneum, which is greater than the action of analogous derivatives already known for this activity.

Consequently, the topical application of these novel derivatives allows the skin to be desquamated and cutaneous ageing to be combated.

Admittedly, it is known from the document U.S. Pat. No. 5,084,270 to use topically, for the treatment of dry skin, amides originating from the condensation of an acidic carbohydrate and a primary amine. However, the prior art neither mentions nor suggests a desquamating action of these products on the skin.

The document WO95/05155 describes lipophilic sugar derivatives, and their use in a cosmetic vehicle as modulators of the synthesis and/or the excretion of fibroblast elastase. However, a desquamating action of carbohydrate derivatives is neither mentioned nor suggested in this document.

SUMMARY OF THE INVENTION

The subject of the present invention is the use in or for the production of a topical composition, in the cosmetic, dermatological and/or pharmaceutical fields, of at least one carbohydrate or carbohydrate derivative corresponding to the formula (I), $$R\text{—}X\text{—}A \qquad (I)$$

in which A is a chain formed of one to twenty carbohydrate units or carbohydrate derivative units, each comprising 3 to 6 carbon atoms, connected to each other, preferably by acetal bridges, it being possible for each of these units to be optionally substituted, for example by a halogen, by an amine function, an acid function, an ester function, a thiol, an alkoxy function, a thioether function, a thioester function, an amide function, a carbamate function or a urea function, R is an alkyl chain or an alkenyl chain, comprising from 4 to 24 carbon atoms, which is branched or linear, it being possible for it to be interrupted by ether bridges, optionally carrying a hydroxyl function, a carboxylic acid function, an amine function, an ester function, an acyloxy function, an amide function, an ether function, a carbamate function or a urea function, X is a function connecting R and A, such as, for example, an amine, ether, amide, ester, urea, carbamate, thioester, thioether or sulphonamide function, for promoting the desquamation of the skin.

A subject of the invention is likewise the use of carbohydrates such as described above for combating cutaneous ageing.

DETAILED DESCRIPTION OF THE INVENTION

Preferentially, R is an alkyl chain or an alkenyl chain, comprising from 4 to 24 carbon atoms, which is branched or linear, optionally carrying a hydroxyl function.

Each of the carbohydrate units forming A can be a sugar or a sugar derivative. For example, each unit forming A can be a reduced sugar, an amino sugar or a sugar carrying a carboxylic acid function.

Among the sugars, or sugar derivatives, which can be involved in the formation of A, mention will be made, for example, of the following products, which are commercially available, optionally in salt form:

N-acetyl-D-galactosamine, N-acetyl-D-glucosamine, N-acetylneuraminic acid, adonitol, β-D-allose, D-altrose, 6-amino-6-deoxy-D-glucose, 1,6-anhydroglucose, arabinic acid, arabinogalactan, D-arabinose, L-arabinose, D,L-arabinose, D-arabitol, L-arabitol, D-cellobiose, D-glucosamine, D-galactosamine, 2-deoxy-D-glucose, 6-deoxy-D-galactose, 6-deoxy-L-galactose, galactitol, mesoerythritol, D-erythroe, D-fructose, D-fucose, L-fucose, D-galactaric acid, galactitol, galactomannan, D-galactono-1,4-lactone, L-galactono-1,4-lactone, D-galactosarmine, D-galactose, L-galactose, D-galacturonic acid, β-gentiobiose, glucamine, D-glucaric acid, D-glucono-1,5-lactone, L-glucono-1,5-lactone, D-glucosamine, D-glucosaminic acid, D-glucuronic acid, L-glucose, D-glucose, isomaltitol, isomaltotriose, isomaltose, lactobionic acid, D-lactose, lactulose, D-lyxose, L-lyxose, lyxosamine, maltitol, D-maltose, maltotetraose, maltotriitol, maltotriose, D-mannosamine, D-mannose, L-mannose, D-melezitose, D-melibiose, D-raffinose, D-raffinose undecaacetate, L-rhamnose, D-ribose, L-ribose, D-ribulose, rutinose, D-sucrose, α-sophorose, sorbitol, D-tagatose, D-talose, D-threose, turanose, D-xylitol, D-xylose, L-xylose and D,L-xylose.

Preferentially, A will be chosen from the following hydrocarbon chains:

D-glucosamine or 2-amino-2-deoxy-D-glucose, D-glucamine or 1-amino-1-deoxy-D-glucitol, N-methylglucamine, D-glucose, D-maltose, sorbitol and maltitol.

Preferentially, R comprises 4 to 16 carbon atoms such as, for example, n-butyl, n-octyl, 2-ethylhexyl and n-dodecyl radicals.

According to the invention, the preferred compositions will comprise at least one product chosen from:

N-butanoyl-D-glucosamine, N-octanoyl-glucosamine, N-octyloxycarbonyl-N-methyl-D-glucamine, N-2-ethyl-hexyloxycarbonyl-N-methyl-D-glucamine, 6O-octanoyl-D-glucose, 6'-O-octanoyl-D-maltose and 6'-O-dodecanoyl-D-maltose.

The preparation of products (I) is well known to the person skilled in the art, and it is possible to refer, for example, to the following documents: FR-A-2703993, FR-A-2715933, EP-A-577506, EP-A-566438, EP-A-485251.

In the compositions according to the invention, the carbohydrate according to (I) or the mixture of carbohydrates according to (I) can be used in a quantity ranging from 0.05 to 20% by weight with respect to the total weight of the composition and in particular in a quantity ranging from 0.2 to 10% and, better, from 0.5 to 5% by weight with respect to the total weight of the composition.

In the compositions which can be used according to the invention, the carbohydrates corresponding to the formula (I) can be combined with other active agents having desquamating properties, such as hydroxy acids, α- or β-keto acids, retinoids and certain sulphonic acids. Such a combination allows the active concentration of the latter to be decreased on account of additive effects. It is thus possible to obtain a composition which is less irritant and less toxic as well as a composition which is more effective than those of the prior art only utilizing these active agents.

The hydroxy acids can be, for example, α-hydroxy acids or β-hydroxy acids, which can be linear, branched or cyclic, saturated or unsaturated. The hydrogen atoms of the carbon chain can, in addition, be substituted by halogens, or halogenated, alkylated, acylated, acyloxylated, alkoxycarbonylated or alkoxylated radicals having from 2 to 18 carbon atoms.

These hydroxy acids are especially glycolic, lactic, malic, tartaric and citric acids and, generally speaking, are fruit acids, 2-hydroxyalkanoic, mandelic and salicylic acids, as well as their alkylated or acylated derivatives such as 5-n-octanoylsalicylic acid, 5-n-dodecanoylsalicylic acid, 5-n-decanoyl-salicylic acid, 5-n-octylsalicylic acid, 5- or 4-n-heptyloxysalicylic acid, 2-hydroxy-3-methylbenzoic acid, or alternatively their alkoxylated derivatives such as 2-hydroxy-3-methoxybenzoic acid.

The retinoids can especially be retinoic acid (all-trans or 13-cis) and its derivatives, retinol (vitamin A) and its esters such as retinol palmitate, retinol acetate and retinol propionate as well as their salts, or alternatively retinal.

By way of example, the hydroxy acids, the keto acids and the retinoids can be introduced into the compositions used according to the invention in a quantity representing from 0.01 to 5% by weight of the total weight of the composition and, better, from 0.1 to 3%.

For the purpose of effectively combating photo-ageing, it is additionally possible to add to the composition used according to the invention one or more hydrophilic or lipophilic complementary solar filters, which are active in the UVA and/or the UVB, optionally comprising a sulphonic function.

A test to measure the efficacy of the carbohydrates was carried out in vitro.

Brysk (Cell and tissue research 253, 657–663, 1988; Differentiation, 32, 230–237, 1986) has shown that haemagglutination constitutes a reliable model for the study of corneocyte cohesion: she has demonstrated haemagglutination due to a glycoprotein of the stratum corneum, as well as inhibition by the same amino sugars at the same time as haemagglutination and as cohesion of the stratum corneum.

The principle of the test lies in the fact that the lectin causes agglutination of the erythrocytes.

The products to be tested, which are prepared at various dilutions, are added to the lectin solutions. The minimum concentration of product allowing the inhibition of haemagglutination caused by the lectin is measured.

The most effective products are those showing an inhibitory activity at the lowest concentration possible.

The results of the tests show activity of the products used according to the invention at concentrations which are much lower than the minimum active concentrations of the products of the prior art tested by way of reference (see further).

A further subject of the invention is a process for cosmetic or dermatological treatment of the skin intended for the desquamation of the skin, consisting in applying to the skin a composition containing at least one carbohydrate of formula (I), in a cosmetically and/or dermatologically acceptable medium.

Another subject of the invention is a process for cosmetic or dermatological treatment of ageing of the skin, consisting in applying to the skin a composition containing at least one carbohydrate such as defined above, in a cosmetically and/or dermatologically acceptable medium.

The composition used according to the invention contains a cosmetically or dermatologically acceptable medium, that is to say a medium compatible with the skin, the nails, the mucous membranes, the tissues and the hair. The composition containing one or more carbohydrates according to (I) can be applied topically to the face, the neck, the hair, the mucous membranes and the nails or any other cutaneous region of the body.

The compositions used according to the invention can be present in all of the forms appropriate for topical application, especially in the form of aqueous, aqueous/alcoholic or oily solutions, of dispersions of the lotion or serum type, of aqueous, anhydrous or oily gels, of emulsions of liquid or semi-liquid consistency of the milk type, obtained by dispersion of a fatty phase in an aqueous phase (O/W) or conversely (W/O), of suspensions or of emulsions of soft, semi-solid or solid consistency of the cream or gel type, of microemulsions or alternatively of microcapsules, of microparticles or of vesicle dispersions of ionic and/or non-ionic type. These compositions are prepared according to the usual methods.

They can likewise be used for the hair in the form of aqueous, alcoholic or aqueous/alcoholic solutions, or in the form of creams, of gels, of emulsions, of foams or alternatively in the form of aerosol compositions also containing a propellant under pressure.

The quantities of the different constituents of the compositions used according to the invention are those conventionally used in the fields under consideration.

These compositions especially form protection, treatment or care creams for the face, for the hands or for the body, protection or care body milks, lotions, gels or foams for the care of the skin and mucous membranes or for cleansing the skin.

The compositions can likewise consist of solid preparations forming soaps or cleansing bars.

In a known manner, the composition used according to the invention can likewise contain adjuvants customary in the cosmetic and dermatological fields, such as hydrophilic or lipophilic gelling agents, hydrophilic or lipophilic active agents, preservatives, antioxidants, solvents, perfumes, fillers and colouring materials. The quantities of these different adjuvants are those conventionally used in the fields under consideration, for example from 0.01% to 20% of the total weight of the composition. These adjuvants, according to their nature, can be introduced into the fatty phase, into the aqueous phase and/or into lipid spherules.

As oils which can be used in the invention, mention may be made of mineral oils (liquid petrolatum), vegetable oils (karite oil, sweet almond oil), animal oils, synthetic oils, silicone oils (cyclomethicone) and fluorinated oils (perfluoropolyethers). It is also possible to use, as fatty materials, fatty alcohols, fatty acids (stearic acid), or waxes (paraffin, carnauba, beeswax).

As emulsifiers which can be used in the invention, mention may be made of Polysorbate 60 and sorbitan stearate sold respectively under the trade names Tween 60 and Span 60 by the company ICI. It is also possible to add co-emulsifiers thereto such as PPG-3 myristyl ether sold under the trade name Emcol 249-3K by the company Witco.

As solvents which can be used in the invention, mention may be made of lower alcohols, especially ethanol and isopropanol, and propylene glycol.

As hydrophilic gelling agents, mention may be made of carboxyvinyl polymers (carbomer), acrylic copolymers such as acrylate/alkylacrylate copolymers, polyacrylamides, polysaccharides such as hydroxypropylcellulose, natural gums (xanthan) and clays, and, as lipophilic gelling agents, mention may be made of modified clays, such as bentones, metallic salts of fatty acids such as aluminium stearates, hydrophobic silica, polyethylenes and ethylcellulose.

As hydrophilic active agents, it is possible to use proteins or protein hydrolysates, amino acids, polyols, urea, allantoin, sugars and sugar derivatives, water-soluble vitamins, starch, bacterial or vegetable extracts, especially of Aloe Vera.

As lipophilic active agents, it is possible to use tocopherol (vitamin E) and its derivatives, essential fatty acids, ceramides or essential oils.

It is possible, inter alia, to combine the carbohydrates according to the invention with active agents intended especially for the prevention and/or for the treatment of cutaneous ailments. Among these active agents, it is possible to mention by way of example:

agents modulating cutaneous differentiation and/or proliferation and/or pigmentation, such as vitamin D and its derivatives, oestrogens such as oestradiol, kojic acid, or hydroquinone;

anti-free radical agents, such as α-tocopherol or its esters, superoxide dismutases, certain metal chelating agents or ascorbic acid and its esters.

It is possible, in addition, to combine with the carbohydrates of the invention antagonists of substance P and/or of CGRP (Calcitonin Gene-Related Peptide or peptide linked to the calcitonin gene) such as Iris Pallida and strontium salts, especially the chlorides and nitrates of strontium, or of antagonists of substance P and/or of CGRP such as those described in the French Patent Applications filed in the name of the Applicant under the numbers 9405537 and 9500900. Such a combination allows a perfect tolerance of these compositions to be guaranteed, even by very sensitive skins.

The cosmetic or dermatological treatment process of the invention can be carried out, especially, by applying the hygienic, cosmetic or dermatological compositions such as those defined above according to the technique of use customary for these compositions. For example: application of creams, of gels, of serums, of ointments, of lotions or of milks to the skin, the scalp, the nails and/or the mucuous membranes.

The following examples illustrate the invention. In these examples, the proportions indicated are percentages by weight.

EXAMPLES

Example 1

Preparation of 6'-O-octanoyl-β-D-maltose

A—Activation of Octanoic Acid

Into a 500 ml round-bottomed flask provided with a system for stirring, a thermometer, and an ascending condenser with a calcium chloride guard are introduced 12.6 g (0.103 mol) of isopropyl chloroformate and 100 ml of tetrahydrofuran. A solution formed of 14.4 g (0.1 mol) of octanoic acid and 10.4 g (0.103 mol) of triethylamine dissolved in 100 ml of tetrahydrofuran is added dropwise to the mixture, which is stirred and cooled to −10° C. During the addition, the temperature is kept between −10° C. and −15° C., and then, at the end, the mixture is allowed to return to ambient temperature and the triethylamine salts are removed by filtration.

B—Preparation of 6'-O-octanoyl-β-D-maltose:

Into a 2 litre round-bottomed flask provided with a stirrer and an ascending condenser are introduced 108 g (0.3 mol) of maltose monohydrate, which are dissolved in 540 ml of pyridine. The solution of activated octanoic acid prepared in A is added to this mixture, and it is stirred at ambient temperature for 17 hours. The reaction mixture is then concentrated in vacuo and then taken up with a mixture of solvents (150 ml of ethyl acetate, 150 ml of heptane, 300 ml of water). The mixture is allowed to settle, and the aqueous phase is isolated and then washed twice with the aid of 250 ml of an ethyl acetate/heptane 1:2 mixture. Finally, the 6'-O-octanoyl-D-maltose is extracted with the aid of an ethyl acetate/butanol 2:1 mixture. After evaporation of the solvents, 13.1 g of 6'-O-octanoyl-β-D-maltose are recovered.

Yield: 28%; Melting point: 226° C.

The $^1$H and $^{13}$C NMR spectra are in keeping with the structure of the product.

Elemental analysis:

|  | C | H | O |
|---|---|---|---|
| calculated: | 51.3 | 7.7 | 41 |
| found: | 51.2 | 7.8 | 40.9 |

Example 2

Preparation of 6-O-octanoyl-α-D-glucose

Into a 2 litre round-bottomed flask provided with a stirrer and an ascending condenser are introduced 72 g (0.4 mol) of anhydrous glucose, which are dissolved in 860 ml of pyridine.

To this mixture is added the activated octanoic acid solution prepared in Example 1-A, and the mixture is stirred at ambient temperature for 17 hours. The reaction mixture is then concentrated in vacuo and then taken up with a mixture of water and acetonitrile and washed three times with an ethyl acetate/heptane 1:1 mixture.

The aqueous phase is isolated and the 6-O-octanoyl-α-D-glucose is extracted with the aid of an ethyl acetate/butanol 2:1 mixture. After evaporation of the solvents, the mixture is taken up in 60 ml of hot acetonitrile. The 6-O-octanoyl-α-D-glucose crystallizes when the solution is allowed to return to ambient temperature. By means of filtration and drying, 14.6 g of 6'-O-octanoyl-α-D-glucose are recovered.

Yield: 48%; Melting point: 128° C.

The $^1$H and $^{13}$C NMR spectra are in keeping with the structure of the product.

Elemental analysis:

|  | C | H | O |
|---|---|---|---|
| calculated: | 54.9 | 8.5 | 36.6 |
| found: | 55.1 | 8.5 | 36.3 |

Example 3

Preparation of N-octyloxycarbonyl-N-methyl-D-qlucamine

In a 1 litre reactor, 24.37 g (0.125 mol) of N-methyl-D-glucamine are dissolved with stirring in 650 ml of water and 850 ml of tetrahydrofuran, then 42 g of sodium bicarbonate (0.5 mol) are added and the temperature of the mixture is brought to 5° C. 24.06 g (0.125 mol) of octyl chloroformate are added dropwise, keeping the mixture at 5° C. for one hour after the addition. The mixture is brought back to ambient temperature, filtered and allowed to settle. The organic phase is recovered, the solvent is evaporated in vacuo and the residue is taken up with 1.5 l of acetone under reflux. The N-octyloxycarbonyl-N-methyl-D-glucamine precipitates when cold. 24 g of product are recovered by filtration and then drying.

Yield: 55%; Melting point: 128° C.

The $^1$H and $^{13}$C NMR spectra are in keeping with the structure of the product.

Elemental analysis: N-octyloxycarbonyl-N-methyl-D-glucamine, ½ $H_2O$

|  | C | H | N | O |
|---|---|---|---|---|
| calculated: | 53.3 | 9.5 | 3.9 | 33.3 |
| found: | 53.3 | 9.6 | 3.9 | 33.2 |

Example 4

Preparation of N-2-ethylhexyloxy-carbonyl-N-methyl-D-glucamine

The procedure is as in Example 3 starting from 0.125 mol of 2-ethylhexyloxycarbonyl chloroformate prepared following Example 1-A.

Yield: 58%; Melting point: 77° C.

The $^1$H and $^{13}$C NMR spectra are in keeping with the structure of the product.

Elemental analysis:

|  | C | H | N | O |
|---|---|---|---|---|
| calculated: | 54.7 | 9.5 | 4.0 | 31.8 |
| found: | 54.5 | 9.6 | 4.0 | 31.7 |

Example 5

Preparation of N-butanoyl-D-glucosamine 15 g of D-glucosamine hydrochloride are dissolved in 150 ml of methanol at ambient temperature. After addition of one equivalent of sodium methoxide and filtration of the sodium chloride formed, 14.8 ml of butyric anhydride are added progressively to the reaction medium, which is then stirred for 3 hours at ambient temperature. A precipitate is formed, which is collected by precipitation and then washed and recrystallized in 130 ml of hot ethanol. 8.8 g of N-butanoyl-D-glucosamine are thus recovered.

Yield: 51%; Melting point: 212° C.

The $^1$H and $^{13}$C NMR spectra are in keeping with the structure of the product.

Elemental analysis:

|  | C | H | N | O |
|---|---|---|---|---|
| calculated: | 48.2 | 7.7 | 5.6 | 38.5 |
| found: | 48.4 | 7.8 | 5.7 | 38.3 |

Tests:

To carry out the tests, rabbit erythrocytes marketed by the company Biomérieux under the reference 72291 are employed. These erythrocytes are used in 50% suspension in water. The lectin used is Banderia simplicifolia isolectin B4, marketed by the company SYGMA.

All the solutions are diluted in phosphate buffer containing calcium and magnesium.

A—Haemagglutination by the Lectin:

The lectin is dissolved in the phosphate buffer at a concentration of 1 mg/ml. 25 µl of phosphate buffer are distributed in all the wells of the microtitre plates. 25 µl of the lectin to be tested are added to the second well. After homogenization, 25 µl from this well are transferred into the following well and so on to obtain successive dilutions. The erythrocytes are diluted to $1/10^e$ (fresh solution) . 5 µl of the suspension and 5 µl of the contents of a well are placed on a plate. After mixing by rotation, it is observed whether or not there is haemagglutination. The latter develops in 5 min at the maximum. The minimum quantity of lectin is thus measured, which allows a clear erythrocyte haemagglutination to be obtained.

B—Inhibition of Haemagglutination:

After having measured the minimum quantity of lectin which allows a clear erythrocyte haemagglutination to be obtained, it is chosen to work at twice the concentration. 25 µl of phosphate buffer are placed in microtitre plates to carry out a negative control. In the other wells are distributed 25 µl of lectin at the determined concentration. In the second well are added 25 µl of phosphate buffer to obtain a positive control. In the third well are placed 25 µl of the carbohydrate derivative to be tested in solution at a concentration of 0.1M. After homogenization, 25 µl from this well are taken and placed in the following well and so on so as to obtain successive dilutions. After having left the lectin and the carbohydrate derivative in contact for 30 min at ambient temperature, 5 µl are placed on a plate and are mixed with 5 µl of erythrocyte suspension. It is observed whether or not there is haemagglutination after agitation by rotation.

C—Results:

The lowest carbohydrate dilution allowing inhibition of haemagglutination to be observed is measured. The result is given as a fraction (corresponding to the dilution) of the initial concentration (0.1M).

1) Products according to the invention

6'-O-octanoyl-D-maltose: ¼

N-2-ethylhexyloxycarbonyl-N-methyl-D-glucamine: 1/16

N-octyloxycarbonyl-N-methyl-D-glucamine: 1/64

2) Products according to the prior art:

N-acetyl-D-glucosamine: no inhibition observed for the undiluted solution: (concentration: 0.1M)

It can thus be concluded from these results that the compounds according to the invention are more effective than the products described in the prior art (Brysk, Cell and tissue research 253, 657–663, 1988).

Composition Examples

These examples illustrate the invention. The proportions indicated are percentages by weight.

| Composition 1: O/W emulsion | |
|---|---|
| Phase A: | |
| 6'-O-octanoyl-D-maltose | 2.5 |
| Sweet almond oil | 14.5 |
| Karite oil | 7.0 |
| PPG-3 myristyl ether (EMCOL 249-3K) | 5.0 |
| Preservative (propylparaben) | 0.1 |
| Polysorbate 60 (TWEEN 60) | 2.5 |
| Sorbitan stearate (SPAN 60) | 2.5 |

| -continued | |
|---|---|
| Composition 1: O/W emulsion | |
| Phase B: | |
| Cyclomethicone | 4.0 |
| Xanthan gum | 0.2 |
| Carboxyvinyl polymer | 0.5 |
| Phase C: | |
| Triethanolamine (neutralizing) | 0.5 |
| Water | 2.0 |
| Phase D: | |
| Preservative (methylparaben) | 0.2 |
| Glycerol | 5.0 |
| Water qsp | 100 |

Procedure:

The constituents of phase A are melted at 85° C., then phase A is cooled to 70° C. and phases B and then C and D are introduced into it with stirring. The mixture is cooled to ambient temperature. A day cream is obtained which causes the desquamation of the skin and thus confers to it a smoother and younger look than before the treatment.

| Composition 2: Gel | |
|---|---|
| N-2-ethylhexyloxycarbonyl-N-methyl-D-glucamine | 5.0 |
| Hydroxypropylcellulose (Klucel H from the company Hercules) | 1.0 |
| Antioxidant | 0.05 |
| Isopropanol | 40.0 |
| Preservative | 0.3 |
| Water qsp | 100 |

A gel is obtained which, on regular application, allows skin spots to be reduced by desquamation.

| Composition 3: Solution for dermatological application | |
|---|---|
| N-octyloxycarbonyl-N-methyl-D-glucamine | 5.00 |
| Antioxidant | 0.05 |
| Ethyl alcohol | 10.00 |
| Preservative | 0.30 |
| Water qsp | 100 |

The application under dermatological control of this solution allows a deep desquamation of the horny layer to be obtained and, thus, an epidermal repair process to be introduced, having as its final therapeutic effect an erasure of spots and dyschromias, a reduction in wrinkles and lines and an improvement in the clinical state of the skin, which takes on the appearance of a younger skin.

This application is made at a rate of one to three weekly sessions for 4 to 6 weeks.

What is claimed is:

1. A method of promoting the desquamation of skin, nails, or mucous membranes, comprising:

applying to the skin, nails, or mucous membranes a desquamation effective amount of at least one carbohydrate or carbohydrate derivative represented by formula (I):

R—X—A     (I)

wherein

A is a chain formed of one to twenty carbohydrate units, wherein each unit comprises 3 to 6 carbon atoms, connected to each other, wherein each unit is optionally substituted by a halogen, by an amine function, an acid function, an ester function, a thiol, an alkoxy function, a thioether function, a thioester function, an amide function, a carbamate function or a urea function, R is an alkyl chain or an alkenyl chain, comprising from 4 to 24 carbon atoms, which is branched or linear, optionally interrupted by ether bridges, optionally carrying a hydroxyl function, a carboxylic acid function, an amine function, an ester function, an acyloxy function, an amide function, an ether function, a carbamate function or a urea function, X is an amine, ether, amide, ester, urea, carbamate, thioester, thioether or sulphonamide function which connects R and A.

2. The method of claim 1, wherein cutaneous ageing is treated.

3. The method of claim 1, wherein the units comprising A are connected to each other by acetal bridges.

4. The method of claim 1, wherein at least one of the units comprising A is selected from the group consisting of reduced sugars, amino sugars and sugars carrying a carboxylic acid function.

5. The method of claim 1, wherein R is an alkyl chain or an alkenyl chain, comprising from 4 to 24 carbon atoms, which is branched or linear, and is substituted with a hydroxyl function.

6. The method of claim 1, wherein the units comprising A are selected from the group consisting of N-acetyl-D-galactosamine, N-acetyl-D-glucosamine, N-acetylneuraminic acid, adonitol, β-D-allose, D-altrose, 6-amino-6-deoxy-D-glucose, 1,6-anhydroglucose, arabinic acid, arabinogalactan, D-arabinose, L-arabinose, D,L-arabinose, D-arabitol, L-arabitol, D-cellobiose, D-glucosamine, D-galactosamine, 2-deoxy-D-glucose, 6-deoxy-D-galactose, 6-deoxy-L-galactose, galactitol, mesoerythritol, D-erythrose, D-fructose, D-fucose, L-fucose, D-galactaric acid, galactitol, galactomannan, D-galactono-1,4-lactone, L-galactono-1,4-lactone, D-galactosamine, D-galactose, L-galactose, D-galacturonic acid, β-gentiobiose, glucamine, D-glucaric acid, D-glucono-1,5-lactone, L-glucono-1,5-lactone, D-glucosamine, D-glucosaminic acid, D-glucuronic acid, L-glucose, D-glucose, isomaltitol, isomaltotriose, isomaltose lactobionic acid, D-lactose, lactulose, D-lyxose, L-lyxose, lyxosamine, maltitol, D-maltose, maltotetraose, maltotriitol, maltotriose, D-mannosamine, D-mannose, L-mannose, D-melezitose, D-melibiose, D-raffinose, D-raffinose undecaacetate, L-rhamnose -D-ribose, L-ribose, D-ribulose, rutinose, D-sucrose, α-sophorose, sorbitol D-tagatose, D-talose, D-threose, turanose, D-xylitol, D-xylose, L-xylose and D,L-xylose.

7. The method of claim 1, wherein A is selected from the group consisting of D-glucosamine, D-glucamine, N-methyl-D-glucamine, D-glucose, D-maltose, sorbitol and maltitol.

8. The method of claim 1, wherein R comprises 4 to 16 carbon atoms.

9. The method of claim 1, wherein (I) is selected from the group consisting of N-butanoyl-D-glucosamine, N-octanoyl-D-glucosamine, N-octyloxycarbonyl-N-methyl-D-glucamine, N-2-ethylhexyloxycarbonyl-N-methyl-D-glucamine, 6-0-octanoyl-D-glucose, 6'-O-octanoyl-D-maltose, and 6'-O-dodecanoyl-D-maltose.

10. The method of claim 1, wherein the carbohydrate or carbohydrate derivative represented by formula (I) is present in a composition, and comprises from 0.05 to 20% by weight with respect to the total weight of the composition.

11. The method of claim 1, wherein the carbohydrate or carbohydrate derivative represented by formula (I) is present in a composition, and comprises from 0.2 to 10% by weight with respect to the total weight of the composition.

12. The method of claim 1, wherein (I) is applied in the form of a topical composition.

13. The method of claim 12, wherein the composition further comprises at least one other active agent having desquamating properties.

14. The method of claim 12, wherein the topical composition further comprises α-hydroxy acids or β-hydroxy acids, which can be linear, branched or cyclic, saturated or unsaturated, it being possible for the hydrogen atoms of the carbon chain to be substituted by halogens, or halogenated, alkylated, acylated, acyloxylated, alkoxycarbonylated or alkoxylated radicals having from 2 to 18 carbon atoms.

15. The method of claim 12, wherein the composition further comprises at least one product selected from the group consisting of fruit acids, salicylic acid, alkylated, acylated or alkoxylated derivatives of salicylic acid, all-trans or 13-cis retinoic acid, derivatives of all-trans or 13-cis retinoic acid, retinol, esters of retinol, salts of retinol, and retinal.

16. The method of claim 12, wherein the composition further comprises at least one product selected from the group consisting of glycolic, lactic, malic, tartaric, citric, mandelic or salicylic acid, 5-n-octanoylsalicylic acid, 5-n-dodecanoylsalicylic acid, 5-n-decanoylsalicylic acid, 5-n-octylsalicylic acid, 5- or 4-n-heptyloxysalicylic acid, 2-hydroxy-3-methylbenzoic acid, 2-hydroxy-3-methoxybenzoic acid, all-trans or 13-cis retinoic acid, retinol, retinol palmitate, retinol acetate, retinol propionate as well as their salts, and retinal.

17. The method of claim 12, wherein the composition comprises, in addition to the carbohydrate(s) represented by formula (I), at least one other compound with desquamating properties, comprising from 0.01 to 5% by weight of the total weight of the composition.

18. The method of claim 12, wherein the composition further comprises at least one hydrophilic or lipophilic complementary solar filter, which is active in the UVA and/or the UVB, and, optionally, comprising a sulphonic function.

19. The method of claim 12, wherein the composition further comprises at least one antagonist of substance P and/or of CORP.

20. The method of claim 12, wherein the composition further comprises at least one strontium salt.

21. The method of claim 20, wherein the composition further comprises at least one chloride or nitrarate of strontium.

22. The method of claim 1, wherein the carbohydrate or carbohydrate derivative represented by formula (I) is 6'-O-octanoyl-D-maltose.

23. The method of claim 1, wherein the carbohydrate or carbohydrate derivative represented by formula (I) is present in a composition, and comprises from 0.5 to 5% by weight with respect to the total weight of the composition.

24. The method of claim 1, wherein the carbohydrate or carbohydrate derivative represented by formula (I) is applied to the skin.

25. The method of claim 1, wherein the carbohydrate or carbohydrate derivative represented by formula (I) is applied to the nails.

26. The method of claim 1, wherein the carbohydrate or carbohydrate derivative represented by formula (I) is applied to the mucous membranes.

27. The method of claim 24, wherein the carbohydrate or carbohydrate derivative represented by formula (I) is applied to the facial skin.

28. The method of claim 24, wherein the carbohydrate or carbohydrate derivative represented by formula (I) is applied to the neck skin.

* * * * *

UNITED STATES PATENT AND TRADEMARK OFFICE
CERTIFICATE OF CORRECTION

PATENT NO. : 6,391,863 B1
DATED : May 21, 2002
INVENTOR(S) : Michel Philippe et al.

It is certified that error appears in the above-identified patent and that said Letters Patent is hereby corrected as shown below:

Column 12,
Line 43, "nitrarate" should read -- nitrate --.

Signed and Sealed this

First Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,391,863 B1 Page 1 of 1
DATED : May 21, 2002
INVENTOR(S) : Michel Philippe et al.

It is certified that error appears in the above-identified patent and that said Letters Patent is hereby corrected as shown below:

<u>Column 12,</u>
Line 39, "CORP" should read -- Calcitonin Gene-Related Reptide --.

Signed and Sealed this

Second Day of September, 2003

JAMES E. ROGAN
*Director of the United States Patent and Trademark Office*